United States Patent [19]

Bell

[11] Patent Number: 5,497,235
[45] Date of Patent: Mar. 5, 1996

[54] INSPECTING AND GRADING APPARATUS FOR HOSIERY AND METHOD OF INSPECTING SAME

[75] Inventor: Cecil R. Bell, Pinnacle, N.C.

[73] Assignee: Monarch Knitting Machinery Corporation, Flushing, N.Y.

[21] Appl. No.: 371,810

[22] Filed: Jan. 12, 1995

[51] Int. Cl.$^6$ .......................... G01N 21/84; G01N 21/00
[52] U.S. Cl. .......................... 356/430; 356/238; 356/239; 356/394; 250/559.39; 250/559.42
[58] Field of Search .......................... 356/237–239, 356/429–431, 394; 250/559.12, 559.15, 559.39, 559, 40–559.42, 559.45–559.46

[56] References Cited

U.S. PATENT DOCUMENTS

| | | | |
|---|---|---|---|
| 3,588,513 | 6/1971 | Takatsuki et al. | 356/430 |
| 3,806,009 | 4/1974 | Glaze, Jr. | 223/112 |
| 4,343,998 | 8/1982 | Mori | 250/559.42 |
| 4,541,351 | 9/1985 | Horita et al. | 223/43 |
| 4,656,463 | 4/1987 | Anders | 340/572 |
| 4,744,035 | 5/1988 | Hashim | 356/431 |
| 4,748,334 | 5/1988 | Kobayashi et al. | 250/559.42 |
| 4,827,395 | 5/1989 | Anders et al. | 364/138 |
| 4,874,241 | 10/1989 | Egea et al. | 356/238 |
| 4,890,924 | 1/1990 | Beckstein | 356/238 |
| 5,133,198 | 7/1992 | Bachmann | 356/241 |
| 5,283,443 | 2/1994 | Norton-Wayne et al. | 250/559.42 |

FOREIGN PATENT DOCUMENTS

| | | |
|---|---|---|
| 0529621 | 3/1993 | European Pat. Off. . |
| 1079585 | 12/1954 | France . |
| 7221847 | 1/1973 | France . |
| 2552966 | 6/1977 | Germany ............... 356/237 |
| 3426056 | 1/1985 | Germany . |
| 57-146137 | 9/1982 | Japan . |
| 60-65173 | 4/1985 | Japan . |

OTHER PUBLICATIONS

*Automated Garment Inspection Using Machine Vision*, L. Norton–Wayne, Leicester Polytechnic, pp. 374–377.
*The Automatic Inspection Myth or Reality?*, J. Yvain, L'Industrie Textile—N° 1199 Mai 1989, pp. 87–90 (also including translation).
*Pantyhose Inspecting Steam Boarding Packaging System*, Model TAS–15GL, Model THP–3GLW, Takatori Corporation, Japan, Jun. 1991.

(List continued on next page.)

*Primary Examiner*—Richard A. Rosenberger
*Assistant Examiner*—Jason D. Eisenberg
*Attorney, Agent, or Firm*—Bell, Seltzer, Park & Gibson

[57] ABSTRACT

A hosiery inspecting and grading apparatus and a method of inspecting hosiery are provided that preferably has a boarding member arranged to mount a completed hosiery article thereon. The boarding member preferably is formed of a translucent material. An optical inspecting system is positioned adjacent the boarding form and is arranged to inspect a completed hosiery article mounted on the boarding member. The optical inspecting system preferably includes at least one light emitter positionally aligned with the boarding member to emit light through a predetermined portion of a completed hosiery article mounted thereon and at least one light detector positionally aligned with the at least one light emitter and the boarding member to detect the presence and absence of light traveling from the light emitter and through the predetermined portion of a completed hosiery article mounted on the boarding member so that presence and absence of defects in a completed hosiery article are thereby determined. The apparatus also has a grading and sorting system positioned downstream from the boarding member and the optical inspecting system and in electrical communication with the optical inspecting system to grade and sort a completed hosiery article responsive to electrical signals representative of presence or absence of defects received from the optical inspecting system.

26 Claims, 6 Drawing Sheets

OTHER PUBLICATIONS

*Pantyhose Inspecting Half-boarding Machine,* Model TAS–20GL, Takatori Corporation, Japan, May 1989.
*Continuous Pantyhose Boarding Machine,* Model TAS–150PO, Takatori Corporation, Sep. 1989.
*Continuous Socks Boarding Machine,* Model TAS–130MO, Takatori Corporation, Jun. 1987.
*Pantyhose Inspecting Half–Boarding Packaging System,* Model TAS–20GL, Model THP–3GL, Model THP–3GL, Takatori Corporation, Jun. 1990.
*Pantyhose Inspecting Steam Boarding Packaging System,* Model TAS–15GL, THP–3GL, Takatori Corporation, Nov. 1990.
*Pantyhose Inspecting Steam Boarding Packaging System,* Model TAS–15GL, Model THP–3GLW, Takatori Corporation, Jun. 1991.
*Continuous Socks Boarding Machine,* Model HAS–800, Takatori Corporation, Dec. 1989.
*Pantyhose Inspecting and Steam Boarding Machine,* Model TAS–15H, Takatori Corporation, Apr. 1994.

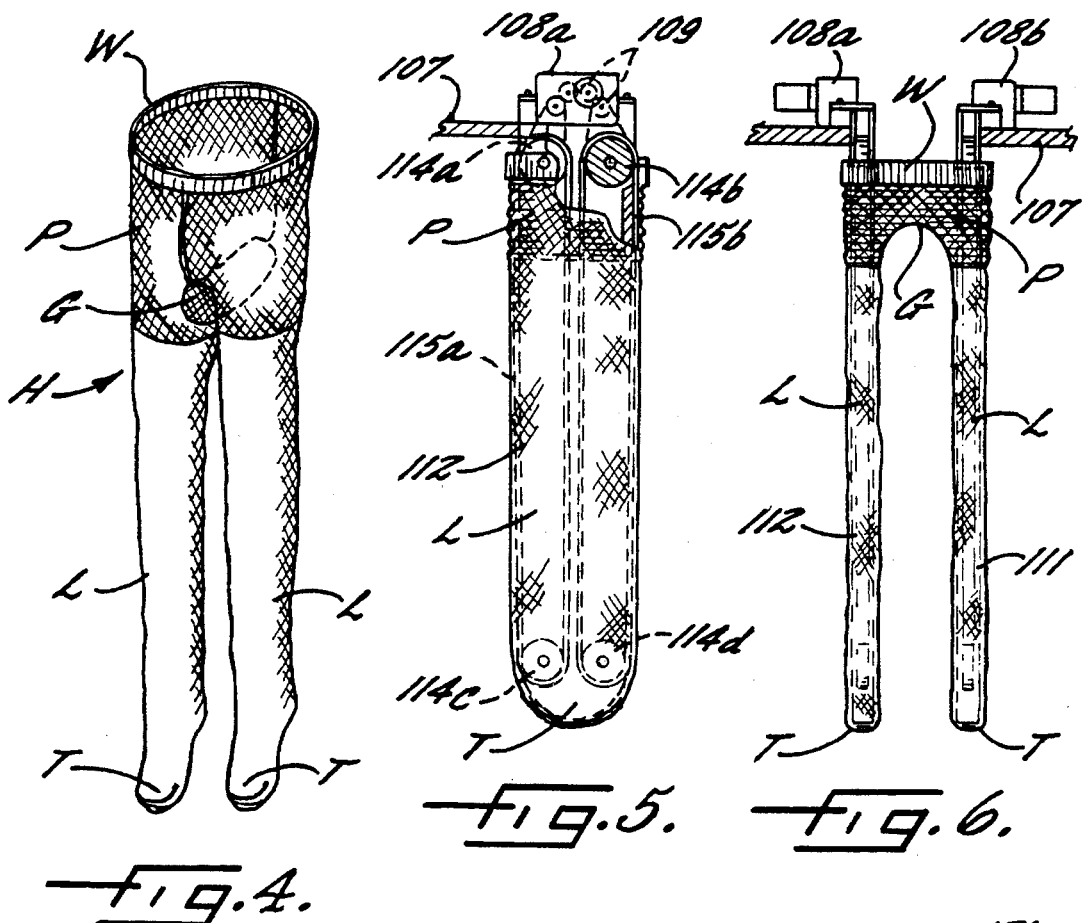
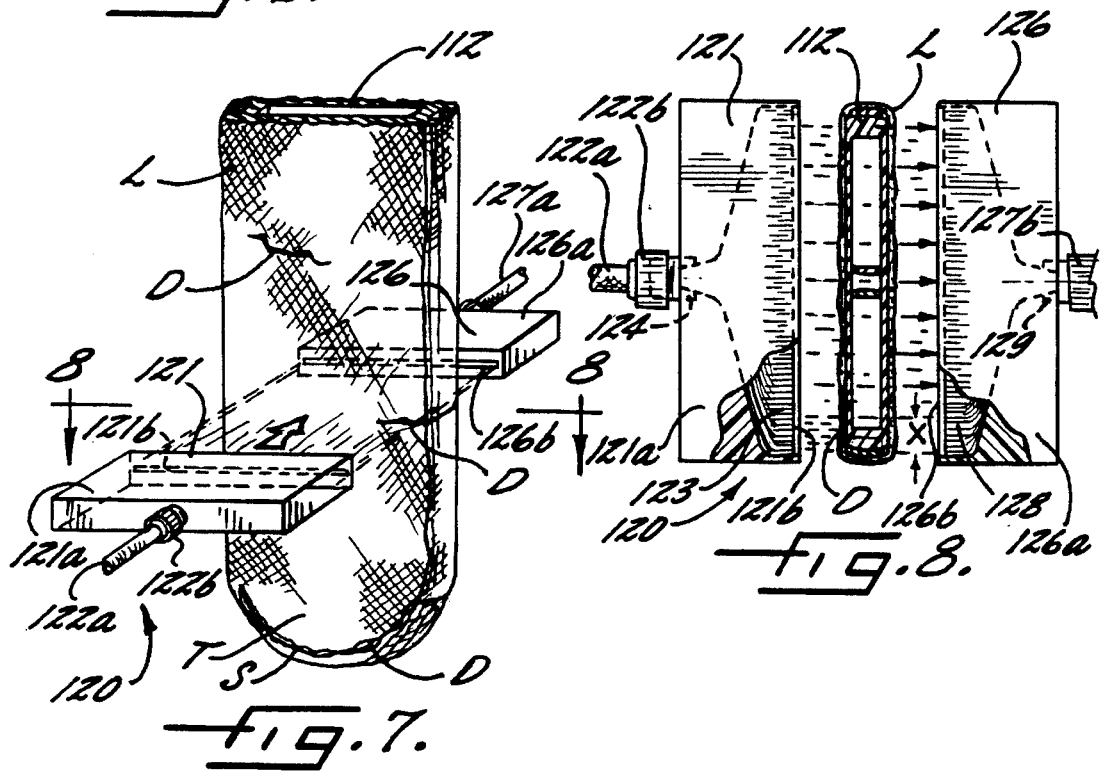

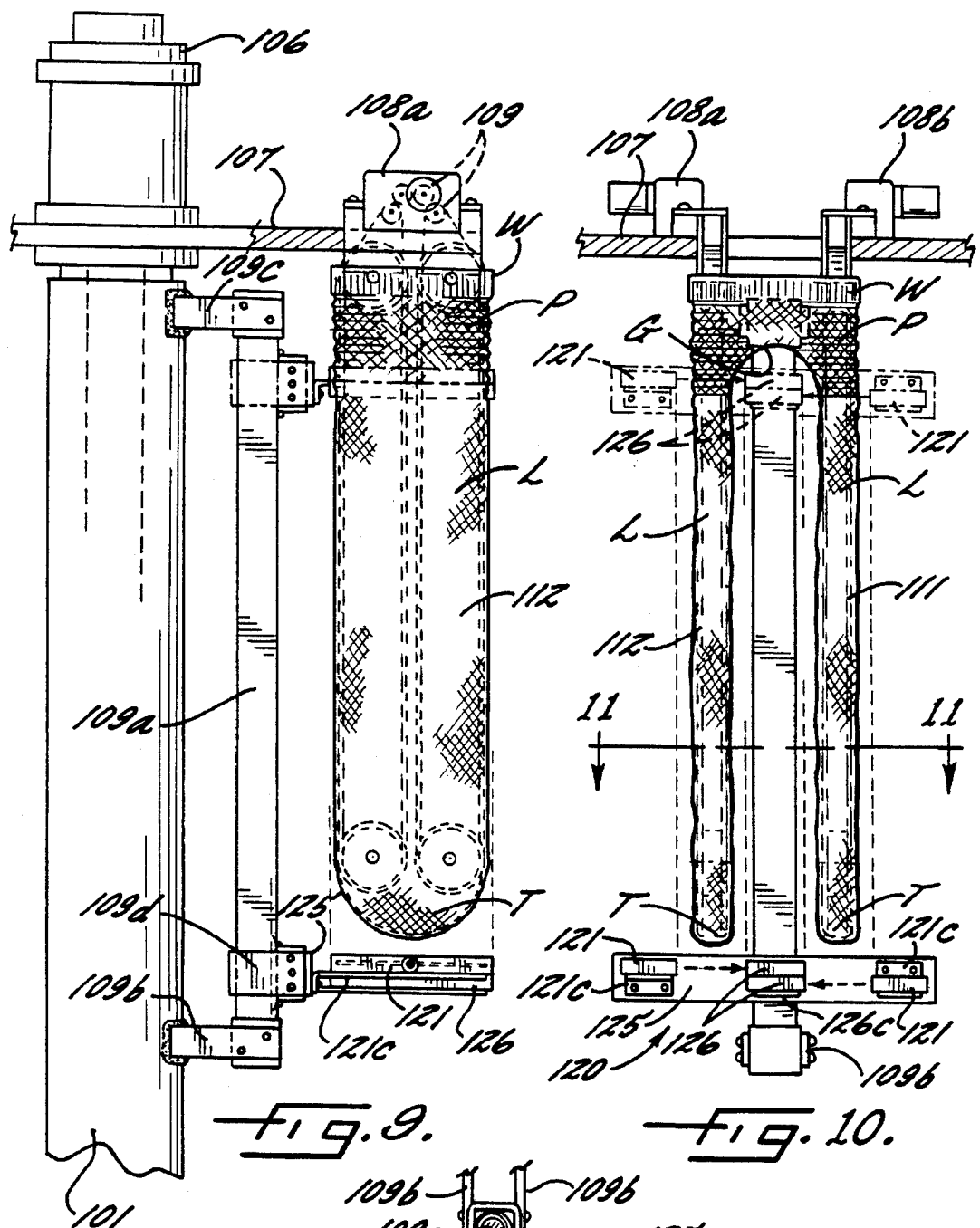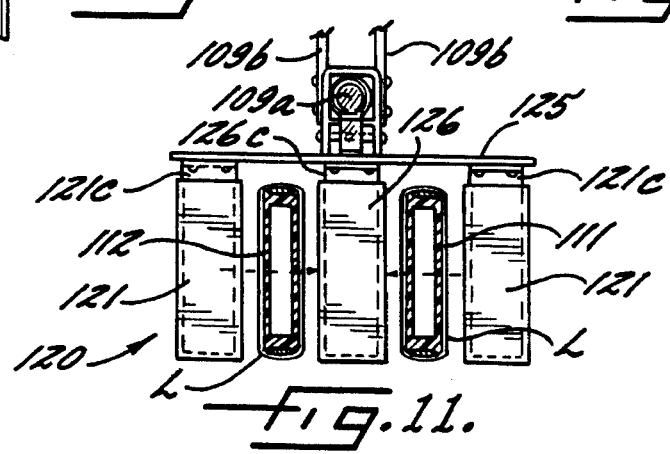

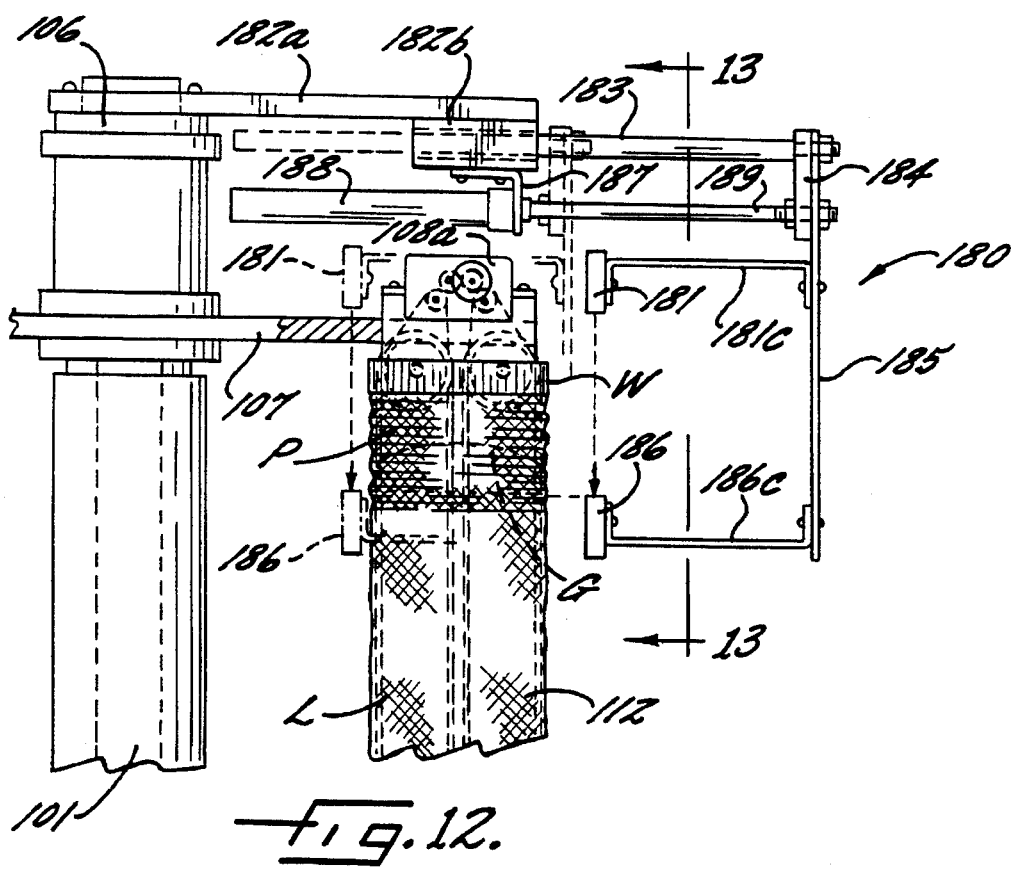
Fig. 12.
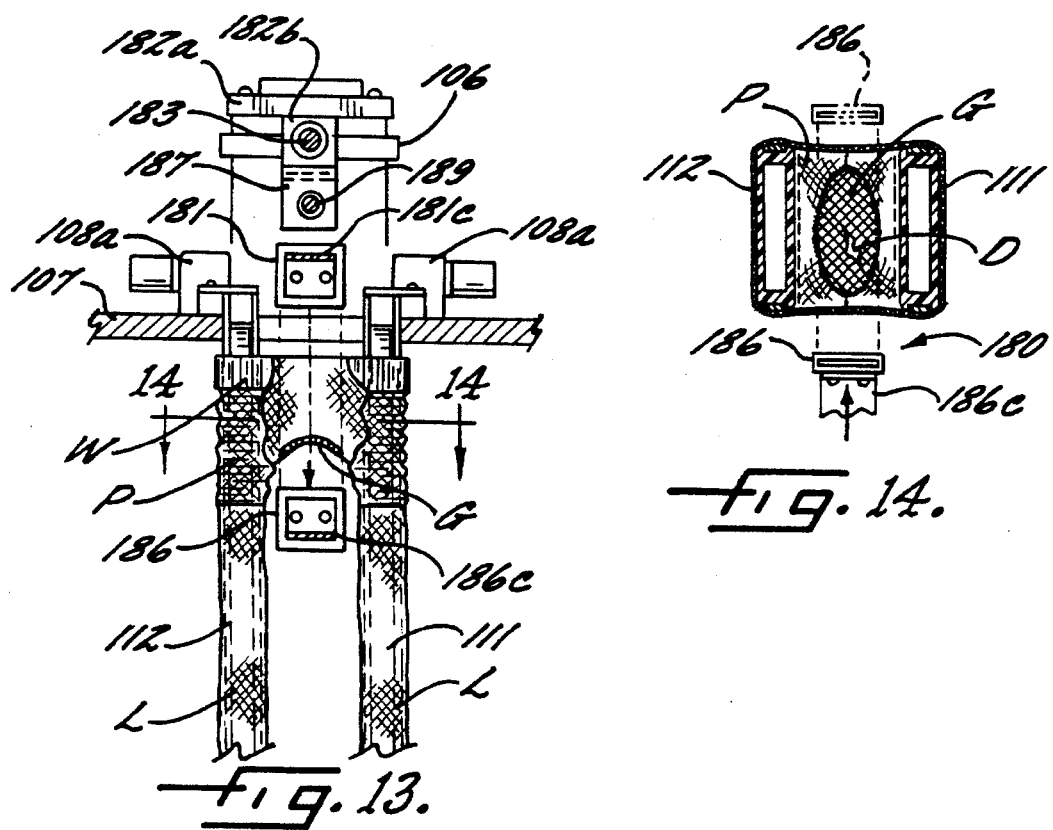
Fig. 13.
Fig. 14.

INSPECTING AND GRADING APPARATUS FOR HOSIERY AND METHOD OF INSPECTING SAME

FIELD OF THE INVENTION

This invention relates to an inspecting and grading apparatus for hosiery articles and a method of inspecting the hosiery articles such as prior to packaging the hosiery for delivery to customers.

BACKGROUND OF THE INVENTION

Over the years, the developments of various synthetic yarns have made possible the production of various knit hosiery articles such as knit leotards, pantyhose, tights, knee-highs, ankle socks, leggings, stockings, and the like. These developments, however, have also resulted in many changes in the methods and procedures employed in the production, packaging, and marketing of the hosiery articles.

The production difficulties precipitated by the popularity of the stretch synthetic yarns used in the production of hosiery also have been further magnified by the increased popularity of pantyhose and other stockings in general. While the increased popularity has produced a need for increased automation in the production process and the accompanying reduction in cost, workable solutions to various problems have not been readily apparent and therefore have not been forthcoming.

In the manufacture of stretch pantyhose from synthetic yarns, for example, it is the conventional practice to knit the garment, either as a unitary structure (including the elastic waistband) or as separate components which are subsequently sewn together, from undyed yarns, and subsequently subjecting the undyed articles to shrinking and dyeing operations. The pantyhose therefore must be knitted, sewn, treated, inspected, transferred, and packaged in a manner that will not damage or unduly stretch the garment. The pantyhose is also preferably flattened and shaped to such a degree as to be easily packaged so that the pantyhose provides an acceptable quality level and an attractive appearance to the purchaser when removed from the package.

One area in the production process where problems have developed over the years in the production of hosiery articles such as pantyhose is in the knitting and sewing operations. For example, operational troubles may often occur during knitting or sewing which results in defects, i.e, picks, faulty or incomplete stitching, in the hosiery articles and thereby may considerably degrade the commercial value of the article. If the defective article reaches the market, it also may seriously blemish the reputation of the producer. Therefore, because these operations are imperfect, the knitted and/or sewn hosiery article is required to be inspected and graded prior to packaging and shipment to retailers and consumers.

Conventionally, the inspection of a completed hosiery article such as pantyhose has been done by visual human inspection of the completed article prior to packaging. This manual visual inspection process, however, is often tedious, time consuming, and includes a varying degree of human judgment even for similar quality standards. Even a certain batch of hosiery, for example, may have a wide variation of quality levels depending on the worker that inspected the completed article. Some operations also employ more than one worker in a particular line operation to inspect the completed hosiery article to ensure that an acceptable quality level is delivered to the retailers and consumers. Despite various inspecting tactics taken during the production process, the industry has been driven toward higher and more uniform production quality at a lower cost which manual labor often fails to provide.

Developments in the inspecting and grading process that have recently occurred have been targeted toward using video or charge coupled device ("CCD") cameras for inspecting a completed hosiery article. Examples of these video camera systems may be seen in European Published Application 0-529-621 titled "Machine For The Quality Control of Knit Products, In Particular Fine-Gauge Pantyhose, Knee Socks, Ankle Socks, And The Like, As Well As Method For The Visual Inspection Of Knit Goods," Japanese Published Application 60-065-173 titled "Fibrous Product Checking Apparatus With Computer Providing Pictorial Information Using Two Television Cameras," and the articles "The Automatic Inspection, Myth Or Reality" by Jean-Michel Yvain in DML Engineering and "Automated Garment Inspection Using Machine Vision" by L. Norton-Wayne in Leicester Polytechnic.

Because the conventional video camera failed to provide the resolution and magnification necessary to accurately inspect a hosiery article for many types of defects, the industry responded with hosiery inspection systems having high resolution video or CCD cameras which are capable of providing a detailed visual image of the hosiery article. These video and CCD cameras, however, are expensive and complex making them less attractive and not economically feasible to many producers of hosiery articles in the industry.

OBJECTS AND SUMMARY OF THE INVENTION

With the foregoing in mind, it is an object of the present invention to provide an accurate apparatus and method of inspecting and grading a completed hosiery article to reduce labor costs and reduce the number of defective hosiery articles in a production process being sent to retailers and consumers.

It is another object of the present invention to provide an apparatus that determines whether a completed hosiery article is defective prior to packaging.

It is also an object of the present invention to provide an apparatus that determines an appropriate and a more uniform quality level of an inspected hosiery article.

It is a yet another object of the present invention to provide a relatively inexpensive and less complex inspecting and grading apparatus that determines a quality level of a completed hosiery article without the use of cameras to visually assist in the inspection process.

It is a further object of the invention to provide a hosiery grading and inspecting apparatus that reduces human judgment in the production of a completed hosiery article.

More particularly, a hosiery inspecting and grading apparatus according to the present invention is provided that has means for mounting a completed hosiery article thereon. The mounting means is preferably formed of a translucent material. Optical inspecting means is positioned adjacent the mounting means for inspecting predetermined portions of a completed hosiery article mounted on the mounting means. The optical inspecting means preferably includes at least one light emitter positionally aligned with a portion of the mounting means to emit light through a hosiery article mounted thereon and at least one light detector positionally aligned with the at least one light emitter and the portion of the mounting means to detect either the presence or absence of light traveling from the light emitter and through predetermined portions of a completed hosiery article mounted on the mounting means so that presence and absence of defects in a completed hosiery article is thereby determined. Grading and sorting means is positioned downstream from the mounting means and the optical inspecting means and in electrical communication with the optical inspecting means for grading and sorting a completed hosiery article responsive to the presence or absence of defects detected by the optical inspecting means.

Also, a hosiery inspecting apparatus for inspecting a leg, a gusset portion, or a toe portion of a leg of a completed hosiery article is further provided according to the present invention. The hosiery inspecting apparatus preferably has a pair of elongate and spaced-apart boarding members arranged to mount a pair of legs of a completed hosiery article thereon so that a gusset portion of the completed hosiery article extends between the pair of elongate and spaced-apart boarding members when the pair of legs are mounted thereon. At least one light emitter is positionally aligned with a portion of a leg, a gusset portion, or a toe portion of the completed hosiery article mounted on the pair of elongate and spaced-apart boarding members. The at least one light emitter preferably is also positioned to travel generally parallel to the leg, the gusset portion, or the toe portion to emit light therethrough. At least one light detector is positionally aligned with the at least one light emitter and a portion of a leg, a gusset portion, or a toe portion of a completed hosiery article positioned therebetween and positioned to travel-generally parallel to the leg, the gusset portion, or the toe portion to detect the presence and absence of light traveling from the light emitter and through the corresponding portion of the completed hosiery article so that presence and absence of defects in a completed hosiery article mounted on the pair of boarding members are thereby determined.

Methods of inspecting and grading a hosiery article additionally are provided according to the present invention. A method of inspecting a hosiery article preferably includes emitting light through a predetermined portion of a completed hosiery article mounted on a translucent boarding member. The presence or absence of light emitted through the predetermined portion of a completed hosiery article is then detected so that presence and absence of defects in a completed hosiery article are thereby determined. A method of inspecting and grading a completed hosiery article further preferably includes mounting a leg of a completed hosiery article onto a translucent and elongate boarding member. Light is then emitted through the boarding member and a portion of the leg, a gusset portion, or a toe portion of the completed hosiery article mounted thereon. Light emitted through the boarding member and the portion of the leg, the gusset portion, or the toe portion of the completed hosiery article mounted thereon is received by a light detector. The completed hosiery article is then graded and sorted responsive to the received light.

The present invention automates the inspecting and grading process for a completed hosiery article so that a higher and more uniform degree of quality may be established with a system that manufactures can afford. The inspecting and grading apparatus also reduces waste, for example, by determining whether a particular hosiery garment may be downgraded, reworked, or sold as a lower quality product which further saves the manufacturer time and money.

BRIEF DESCRIPTION OF THE DRAWINGS

Some of the objects and advantages of the present invention having been stated, others will become apparent as the description proceeds when taken in conjunction with the accompanying drawings in which:

FIG. 4 illustrates an example of a hosiery article in the form of knit pantyhose to be inspected and graded by a hosiery inspecting and grading apparatus according to the present invention;

FIG. 5 illustrates a side elevational view of a boarding member of a hosiery inspecting and grading apparatus having a hosiery article mounted thereon according to the present invention;

FIG. 6 illustrates a front elevational view of a boarding member of a hosiery inspecting and grading apparatus according to the present invention;

FIG. 7 illustrates a fragmentary perspective view of a boarding member having a hosiery article mounted thereon and an optical inspector of a hosiery inspecting and grading apparatus according to the present invention;

FIG. 8 illustrates a sectional view of a boarding member having a hosiery article mounted thereon and an optical inspector of a hosiery inspecting and grading apparatus according to the present invention taken along line 8—8 of FIG. 7;

FIG. 9 illustrates a side elevational view of a hosiery inspecting and grading apparatus having a hosiery article mounted thereon according to the present invention;

FIG. 10 illustrates a front elevational view of a hosiery inspecting and grading apparatus having a hosiery article mounted thereon according to the present invention;

FIG. 11 illustrates a sectional view of a hosiery inspecting and grading apparatus having a hosiery article mounted thereon according to the present invention taken along line 11—11 of FIG. 10;

FIG. 12 illustrates a fragmentary perspective view of an optical inspector positioned to inspect a toe portion of a completed hosiery article mounted on a hosiery inspecting and grading apparatus according to the present invention;

FIG. 13 illustrates a top fragmentary view of an optical inspector system positioned to inspect a toe portion of a completed hosiery article mounted on a hosiery inspecting and grading apparatus according to the present invention taken along line 13—13 of FIG. 12;

FIG. 14 illustrates a sectional view a hosiery inspecting and grading apparatus having a hosiery article mounted thereon according to the present invention taken along line 14—14 of FIG. 13;

DETAILED DESCRIPTION

The present invention will now be described more fully hereinafter with reference to the accompanying drawings in which typical preferred embodiments are shown. This invention, however, may be embodied in many different forms and should not be construed as limited to the illustrated embodiments set forth herein; rather, these embodiments are provided so that this disclosure will be thorough and complete and will fully convey the scope of the invention to those skilled in the art. Like numbers refer to like elements throughout.

Figure 1:
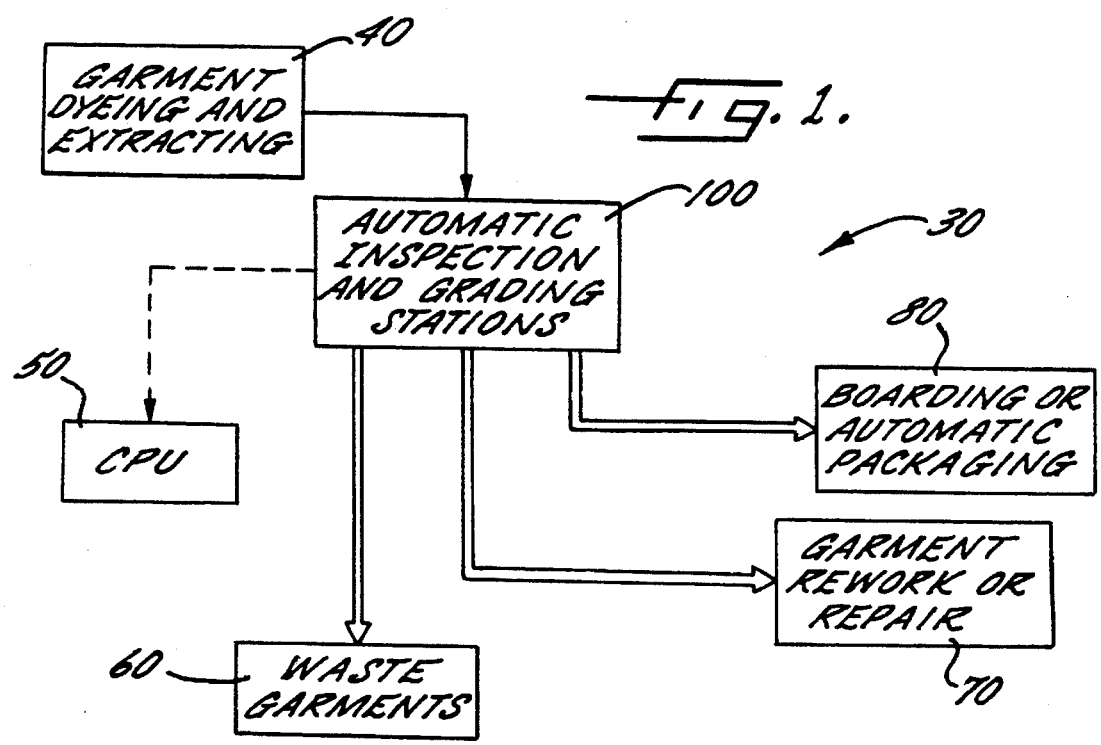
FIG. 1 illustrates a schematic view of a hosiery inspecting and grading apparatus positioned in a hosiery production process according to the present invention.
Figure 2:
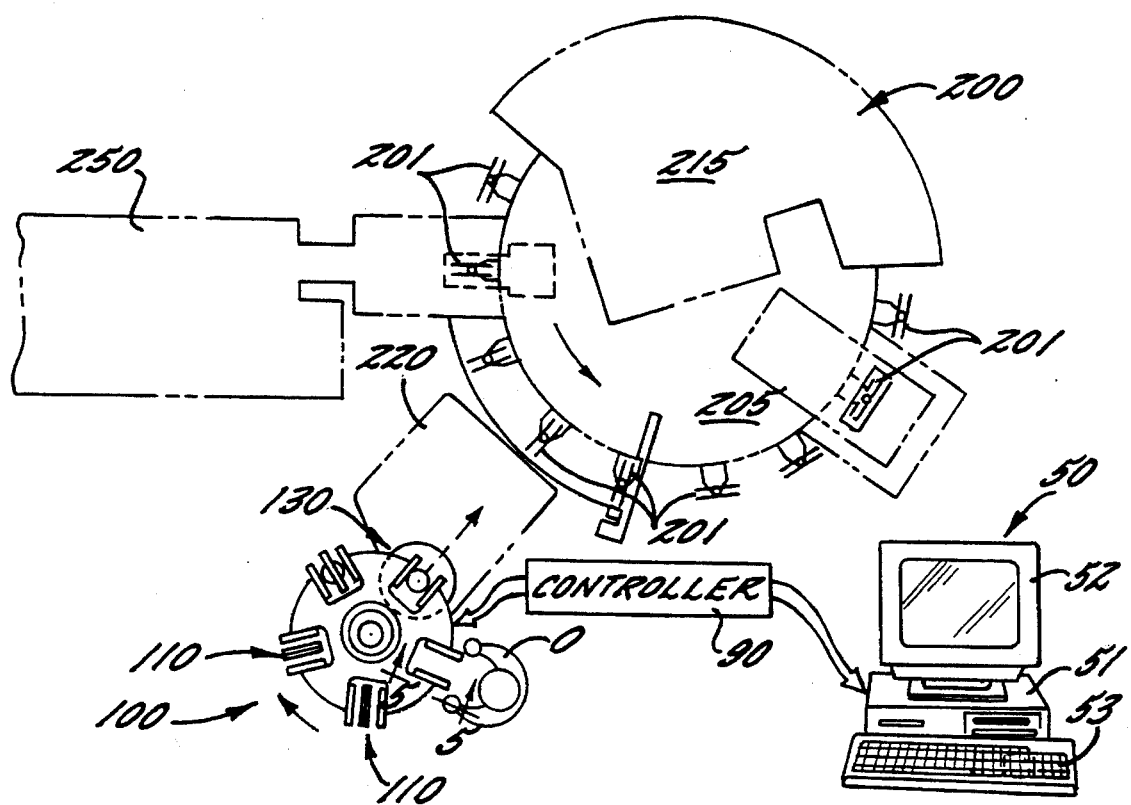
FIG. 2 illustrates a schematic view of a hosiery inspecting and grading apparatus positioned prior to boarding and packaging in a hosiery production process according to the present invention.

FIGS. 1–2 schematically illustrate a hosiery inspecting and grading apparatus 30 according to the present invention positioned in an operational relationship in hosiery production. As illustrated, the hosiery inspecting and grading apparatus 30 is preferably positioned downstream from a garment dyeing and extracting apparatus 40 so that a completed hosiery article H, such as knit leotards, pantyhose, tights, stockings, leggings, ankle socks, or the like, sometimes referred to generally as pantyhose, panty garments, or stockings (see e.g., FIG. 4), is transported to the automatic inspection and grading stations 100 of the invention. The inspection and grading stations 100 in combination with a computer system and/or controller 90 having a central processing unit ("CPU") 50 as illustrated and means for sorting the inspected and graded garments 130 preferably together form a hosiery inspecting and grading apparatus 30 according to the invention.

Figure 3:
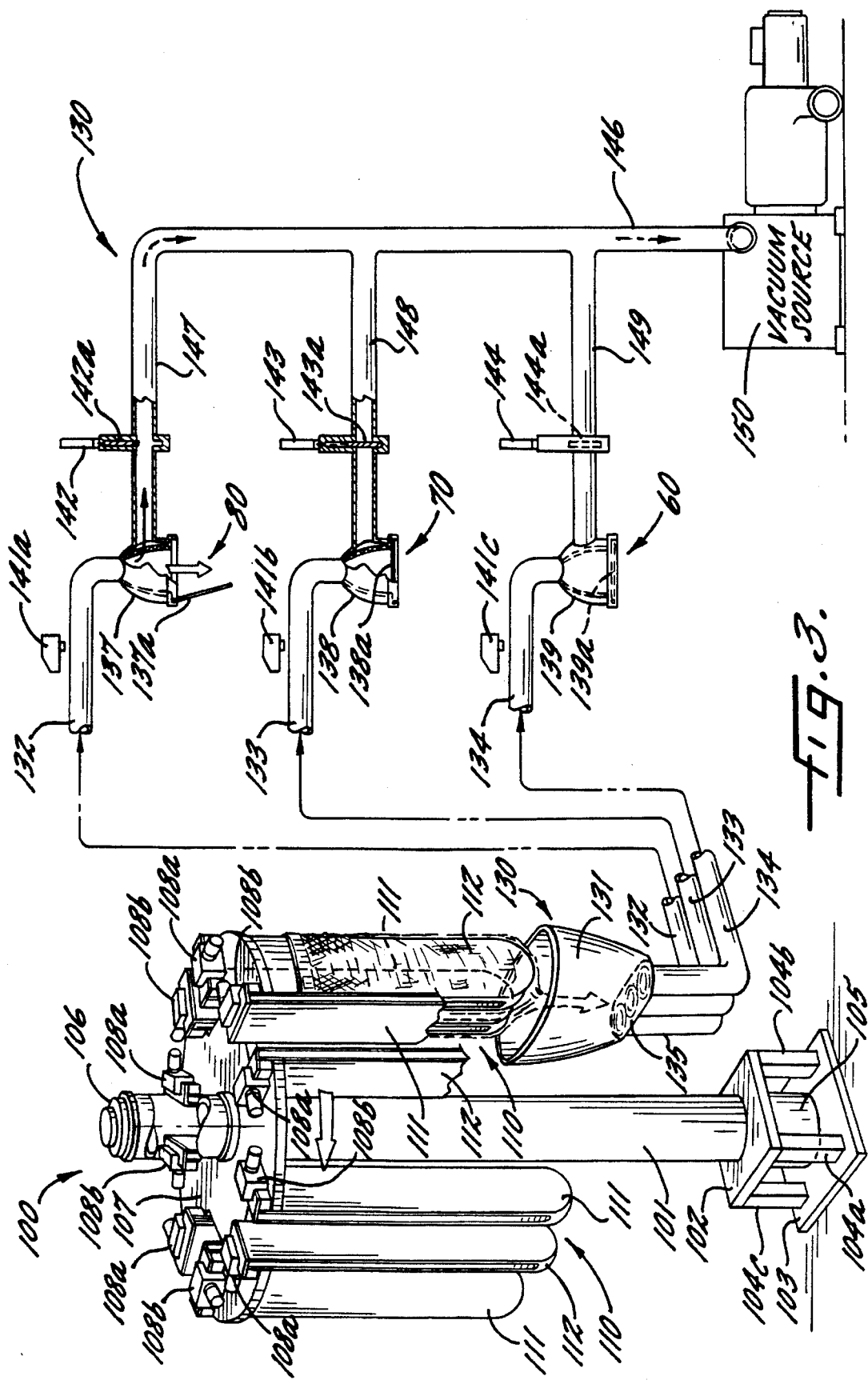
FIG. 3 illustrates a perspective view of a hosiery inspecting and grading apparatus according to the present invention.

As illustrated in FIGS. 2–3, an operator O preferably manually mounts a completed hosiery article H onto one of a plurality of boarding members 110 of the inspecting and grading stations 100. Each of the plurality of boarding members 110 is preferably formed of a pair of elongate and space-apart boarding forms or members 111, 112 (See FIGS. 3 and 6). The completed hosiery article H preferably is then inspected for defects D therein by an optical inspecting means, i.e., optical inspector, of the hosiery inspecting and grading apparatus 30 of the present invention. The inspected hosiery article H is then graded and sorted based on predetermined quality levels, e.g., into one of at least three predetermined quality groups, and transported to either waste garments 60, garment rework or repair 70, i.e., seconds, irregulars, downgrades, or repairs, or boarding or automatic packaging 80, i.e, first quality. The seconds or downgrades, for example, may even have multiple levels of quality categories from top quality to varying degrees of lower quality and/or waste.

The controller 90 is positioned in electrical communication with the optical inspecting means and is arranged to determine the presence and absence of defects D in a hosiery article responsive to electrical signals representative of the presence or absence of light received from at least one light detector 121, 161, 181 of the optical inspecting means. (See FIGS. 2, 7–8, 12–13, and 15–17). The controller 90 may for a part of or positioned separately from a computer system having a CPU 50 such as illustrated and may be a hardware and/or software implementation as understood by those skilled in the art.

The computer system 50 also preferably includes a memory device 51, a keyboard 53 connected to the memory device 51, and a display 52, such as a cathode ray tube ("CRT"), also connected to the memory device 51. As understood by those skilled in the art, the memory device 51 of the computer system 50 preferably includes a CPU or microprocessor operating under stored program control and/or read-only memory and random access memory devices.

The computer system 50, as illustrated in FIG. 2, provides operator 0 interaction, i.e., responsive to electrical command signals, and feedback with the inspecting 100 and grading and sorting 130 stations of the apparatus 30. The computer system 50 further provides means of recording or storing data related to defects in the inspected hosiery articles in a production process which, in turn, provides data for a manufacturer to use in measuring various production performance criteria, i.e., quality, throughput, number of reworks or downgrades, locate production problems, and the like. This data can be further processed by the computer system 50 for predetermined purposes as well as communicated to another data processing and/or displaying apparatus For example, if the inspected hosiery article H is determined to be of first quality based upon predetermined H quality standards or levels, then responsive to predetermined electrical signals received from the controller 90. The inspected hosiery article H is preferably transported first to a boarding apparatus 200 and second to a packaging apparatus 250. The inspected hosiery article H is preferably transported from the hosiery inspecting and grading apparatus 30 to a boarding chamber 205 via an auto-loader 220 onto one of a plurality of boarding blanks 201 positioned to receive the inspected hosiery article H as best illustrated in FIG. 2. The boarded hosiery article H is then further prepared and transported through a drying chamber 215 prior to final packaging 250.

As best illustrated in the perspective view of FIG. 3, a hosiery inspecting and grading apparatus 30 according to the present invention preferably has a plurality of inspecting stations 100 arranged for mounting a plurality of completed hosiery articles thereon. The plurality of inspecting stations 100 preferably has a base member 101 illustrated in the form of a cylindrical mounting post. The base member 101 has upper 106 and lower 105 end portions. A lower base frame supports the base member 101 in an upright position and is formed by a pair of rectangular and spaced-apart lower plate members 102, 103 and a plurality of leg members 104a–104d vertically extending therebetween. The upper end portion 106 of the base member 101 preferably has an annular base plate 107 secured thereto for rotational movement about the upper end portion 106 of the base member 101.

A plurality of pairs of elongate and spaced-apart boarding members 111, 112 have upper portions thereof pivotally mounted to respective mounting brackets 108a, 108b secured to the base plate 107 so that rotation of the base plate 107 about the upper end portion 106 of the base member 101 correspondingly rotates the boarding members 111, 112. Each of the pair of elongate and spaced-apart boarding members 111, 112 extends downwardly from the base plate 107 secured to the upper end portion 106 of the base member 101 and is respectively arranged to mount a pair of legs L of a hosiery article such as pantyhose H thereon so that a gusset portion G of the pantyhose H extends between the pair of elongate and spaced-apart boarding members 111, 112. Each of the boarding members 111, 112 are also preferably formed of a translucent material so that during inspection light can pass through the boarding member 111, 112 and a portion of a completed predetermined hosiery article mounted thereon.

FIG. 4 illustrates an example of a completed hosiery article in the form of pantyhose H to be inspected and graded by the apparatus 30 of the invention. The pantyhose H has a pair of legs L which each have a toe portion T at a lower end thereof. A panty portion P is secured to upper ends of the legs L. The panty portion P also preferably includes a waistband W and a gusset portion G as illustrated.

As illustrated in FIGS. 5–6, each of the boarding members 111, 112 preferably include front and back surfaces and a pair of mounting belts 115a, 115b rotatably positioned therebetween. The mounting belts 115a, 115b are each rotatively mounted to a respective pair of pulleys or wheels 114a, 114b, 114c, 114d also positioned between the front and back surfaces of the boarding members 111, 112. The pulleys 114a, 114b are driven by driving gears and/or motors 109 preferably positioned within or closely associated with the mounting brackets 108a, 108b. The mounting belts 115a, 115b are positioned so that rotation of the belts 115a, 115b in one direction, i.e., clockwise, assists the operator O in the mounting of the completed hosiery article H onto the boarding members 111, 112. Also, the rotation of the belts 115a, 115b in the opposite direction, i.e., counter-clockwise, assists in the removal of the hosiery article H from the boarding members 111, 112. The directional rotation is preferably controlled by the controller 90 but may also be manually adjusted and/or controlled.

As best illustrated in FIGS. 7–17, a hosiery inspecting and grading apparatus according to the present invention has optical inspecting means, i.e., optical inspector, which preferably includes a combination of a leg inspector 120 (see FIGS. 7–11), a gusset inspector 180 (see FIGS. 12–14), and a toe inspector 160 (see FIGS. 15–17) but may include only one or two of the leg inspector 120, the gusset inspector 180, and/or the toe inspector 160, e.g., depending on the production application. The leg inspector 120, the gusset inspector 180, and/or the toe inspector 160 may be mounted in various combinations or configurations to the base member 101 at either the same or different inspecting stations 100 according to the present invention. Preferably, however, the leg inspector 120 and the gusset inspector 180 are mounted at the same inspecting station, and the toe inspector 160 is preferably mounted at a separate inspecting station.

The leg inspector 120 of the optical inspecting means has at least one light emitter 121 positionally aligned with at least one, i.e., 112, of the boarding members 111, 112 and positioned to vertically travel generally parallel to a front surface of the boarding member 112. The light emitter 121 emits light onto and through the front surface of the boarding member 112 and a portion of a leg L of pantyhose H when mounted thereon.

The light emitter 121 of the leg inspector 120 preferably has a housing 121a having a light emitting diode 124 positioned therein and a plurality of optical fibers 123 optically aligned with the light emitting diode 124. The optical fibers 123 are arranged to transmit light received from the light emitting diode 124 to a portion of leg L of a completed hosiery article H mounted on the boarding member 112. The light from the optical fibers 123 preferably travels through an elongate slit 121b formed in an end of the housing 121a and is transmitted toward and through the boarding member 112 and a portion of the leg L of the hosiery article H mounted thereon.

The leg inspector 120 of the optical inspecting means also preferably includes a light detector 126 positionally aligned with the light emitter 121 and at least one of the plurality of boarding members 111, 112 and positioned to vertically travel generally parallel to a back surface of at least one elongate boarding member 112. The light detector 126 detects the presence and absence of light traveling from the light emitter 121 and through the boarding member 112 and the portion of the pantyhose H mounted thereon, as illustrated by the directional arrows of FIGS. 7–8 and 11, so-that presence and absence of defects D, such as picks of various sizes (see FIGS. 7–8), in a completed pantyhose H mounted on the boarding member 112 are thereby determined.

The light detector 126 likewise preferably has a housing 126a and an optical receiver 129 positioned within the housing 126a. A plurality of optical fibers 128 are arranged to receive light transmitted form the light emitter 121. The optical fibers 128 preferably are arranged along a corresponding elongate slit 126b in an end portion of the housing 126a.

More particularly as illustrated in FIG. 8, for example, the absence of light received in a portion of light detector 126 preferably corresponds to a defect D or pick detected in a portion of the leg L of the hosiery article H. The presence of light accordingly corresponds to either no defect D detected or a defect D or pick of such a small size as to be acceptable, not noticeable, or otherwise prevent the hosiery article H from obtaining a predetermined quality level. Because the light emitter 121 and the light detector 126 preferably have an array of optical fibers linearly dispose across corresponding horizontal slits 121b, 126b, the presence or absence of light is readily detected by the leg inspector 120. It will also be understood by those skilled in the art that various other arrays, such as a plurality of linearly disposed individual light emitting diodes and/or optical receivers, Or other stacked or vertically orientations also are taught according to the leg inspector 120 of the invention.

The light emitter 121 and the light detector 126 of the leg inspector 120, as well as those of the gusset inspector 180 and the toe inspector 160 further described herein, preferably are each respectively in electrical communication with and connected to the controller 90 such as by electrical cable 122a, 126a and connectors 122b, 126b as illustrated. The light emitters 121 and the light detectors 126 of the optical inspecting means forming the leg inspector 120, the gusset inspector 180, and/or the toe inspector 160 are preferably like the 500 series DC scanners, i.e., SM53E and SM53R, manufactured by Banner Engineering Corporation of Minneapolis, Minn. and also preferably include Banner AC-coupled amplifiers or similar circuitry positioned in electrical communication with the light emitter 121 and the light detector 126 as understood by those skilled in the art.

The light emitter 121 and light detector 126 corresponding to each boarding member 111, 112 of the apparatus 30 further are preferably mounted in a spaced-apart relation by respective mounting brackets 121c, 126c secured to the respective housings 121a, 126a to a mounting plate 125. The mounting plate 125 is secured to a coupling 109d which is slidably positioned along a vertically-extending mounting member 109a secured to and extending generally parallel to the base member 101. The vertically-extending mounting member 109a is secured to the base member 101 by lower and upper mounting brackets 109b, 109c secured to respective ends thereof.

Also, as illustrated in FIGS. 10 and 11, each boarding member 111, 112 preferably has at least one light emitter 121 and a corresponding at least one light detector 126 mounted for detecting defects in the leg L of the hosiery article H. The mounting arrangement of the light emitter 121 and light detector 161 respectively may include more than emitter and/or detector. As also understood by those skilled in the art, these emitters and detectors may also be customized for sizing and positioning for specific applications according to the hosiery inspecting and grading apparatus of the present invention.

The mounting arrangement of the leg inspector 120 as illustrated provides a scanning-type motion as the light emitters 121 and the light detectors 126 vertically travel up and down the leg L of the hosiery article H as illustrated by the phantom lines in FIGS. 9 and 10. The light detectors 126 preferably are mounted closely adjacent each other on the mounting plate 125 and extend between the pair of elongate and spaced-apart boarding members 111, 112.

As best illustrated in FIGS. 12–14, the optical inspecting means also preferably includes a gusset inspector 180 having a light emitter 181 arranged to emit light through a gusset portion G extending between a pair of legs L of pantyhose H mounted on the pair of boarding members 111, 112. A light detector 186 is positionally aligned with the light emitter 181 and arranged to detect light traveling from the light emitter 181 and through a gusset portion G of the pantyhose H so that presence and absence of defects D, such as holes, faulty or incomplete stitching, in the gusset portion G are thereby determined. The gusset inspector 180 is also preferably positioned in electrical communication with the controller 90.

As illustrated in FIG. 14, for example, the presence of light received in a portion of light detector 186 preferably corresponds to a defect D or hole detected in the gusset portion 8 of the hosiery article H. The absence of light accordingly corresponds to either no defect D detected or a defect D or hole of such a small size as to be acceptable, not noticeable, or otherwise prevent the hosiery article H from obtaining a predetermined quality level. Because the light emitter 181 and the light detector 186, like those of the leg inspector 120, preferably have an array of optical fibers linearly dispose across corresponding horizontal slits 181b, 186b in a housing 181a, 186a thereof, the presence or absence of light is readily detected by the gusset inspector 180. It will also be understood by those skilled in the art that various other arrays, such as a plurality of linearly disposed individual light emitting diodes and/or optical receivers, or other stacked or vertically orientations also are taught according to the gusset inspector 180 of the optical inspecting means of the present invention.

The light emitter 181 and the light detector 186 of the gusset inspector 180, as best illustrated in FIGS. 12–13, are preferably mounted on respective horizontally extending plate members 181a, 186a and secured to a vertically extending plate member 185 to thereby form a generally C-shape configuration. The vertically extending plate member 185 is secured to a mounting plate 184 which, in turn, is secured to a piston 189 which reciprocates into a piston chamber of a cylinder 188 to provide a generally-horizontal scan of the gusset portion G of the pantyhose H. Portions of the mounting plate 184 are also secured to a horizontally-extending mounting rod 183. The cylinder 188 is secured to a lower plate member 182b, and the mounting rod 184 is slidably connected to the lower plate member 182b as illustrated. The lower plate member 182b preferably is secured to an upper plate member 182a, and the upper plate member 182a preferably is secured to the upper end portion 106 of the base member 101.

Figure 15:
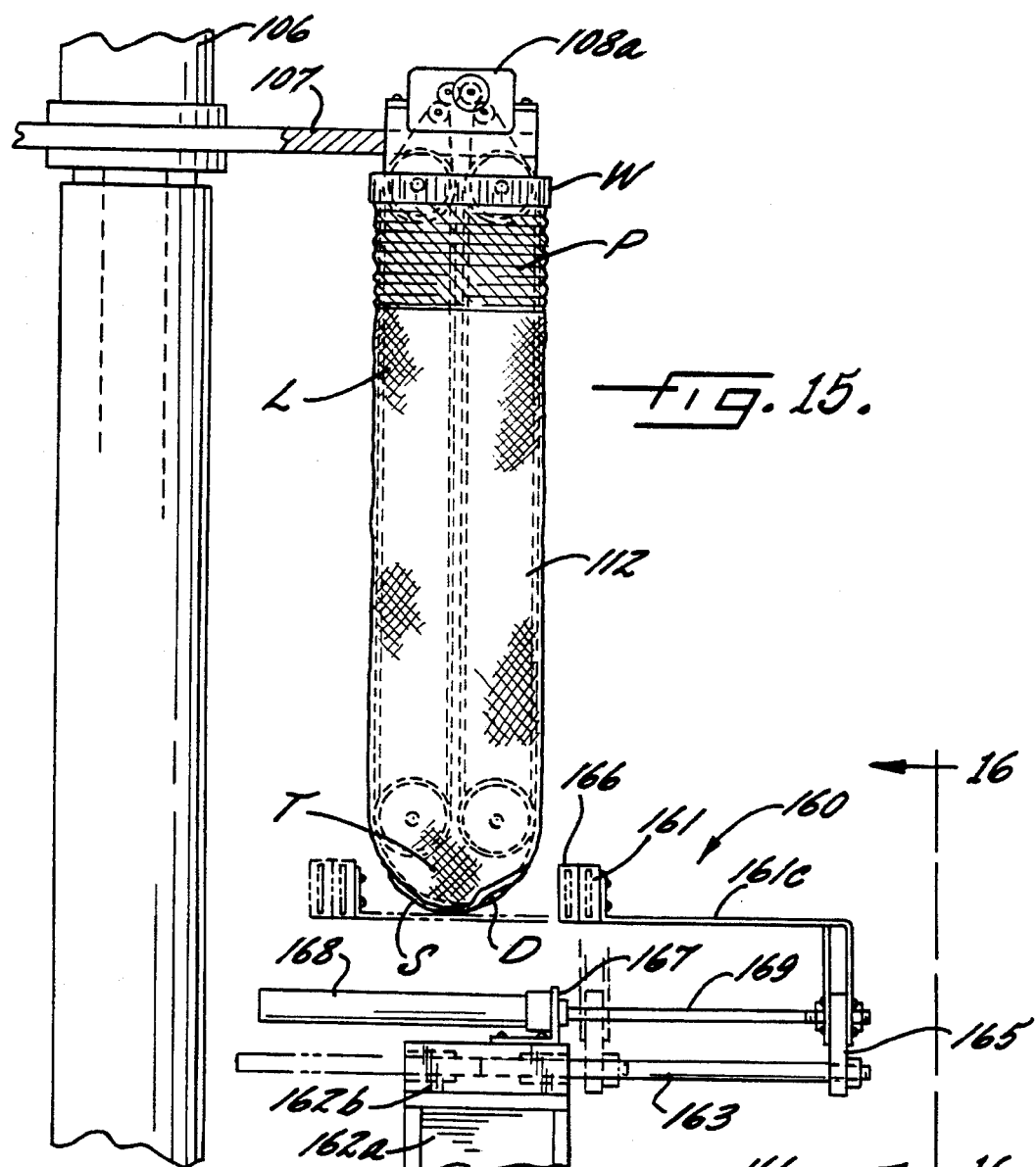
FIG. 15 illustrates a side elevational view of a hosiery inspecting and grading apparatus positioned to inspect a gusset portion of a hosiery article mounted thereon according to the present invention.
Figures 16, 17:
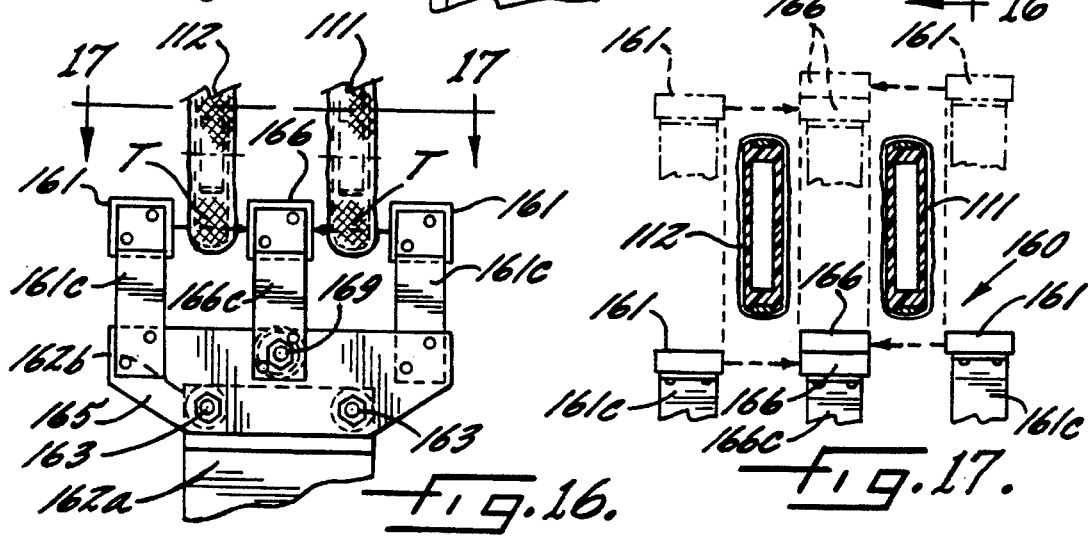
FIG. 16 illustrates a front elevational view of a hosiery inspecting and grading apparatus according to the present invention taken along line 16—16 of FIG. 15.
FIG. 17 illustrates a sectional view of a hosiery inspecting and grading apparatus according to the present invention taken along line 17—17 of FIG. 16.

As best illustrated in FIGS. 15–17, the optical inspecting means further preferably includes a toe inspector 160 having a light emitter 161 arranged to emit light through a toe portion T of a leg L of pantyhose H mounted on the boarding member. A light detector 166 is positionally aligned with the light emitter 161 and arranged to detect light traveling from the light emitter 161 and through a toe portion T of pantyhose H mounted on the boarding member 112 so that presence and absence of defects D, such as holes, faulty or incomplete stitching S, in the toe portion T are thereby determined.

As illustrated in FIGS. 15–16, and for example like the gusset inspector 180, the presence of light received in a portion of light detector 166 preferably corresponds to a defect D or hole detected in the toe portion T, and more particularly the stitching S which closes the toe portion T, of the hosiery article H. The absence of light accordingly corresponds to either no defect D detected or a defect D or hole of such a small size as to be acceptable, not noticeable, or otherwise prevent the hosiery article H from obtaining a predetermined quality level. Because the light emitter 161 and the light detector 166, like those of the leg inspector 120 and the gusset inspector 180, preferably have an array of optical fibers linearly dispose across corresponding horizontal slits 161b, 166b in a housing 161a, 166a thereof, the presence or absence of light is readily detected by the toe inspector 160. It will also be understood by those skilled in the art that various ether arrays, such as a plurality of linearly disposed individual light emitting diodes and/or optical receivers, or other stacked or vertically orientations also are taught according to the toe inspector 160 of the optical inspecting means of the present invention.

The toe inspector 160 of the optical inspecting means preferably has a pair of light emitters 161 and a pair of light detectors 166 thereof positionally aligned and mounted to horizontally-extending mounting plates 161c, 166c. The mounting plates 161c, 166c are secured to a plate member 165 which has a piston rod 169 also secured thereto. The piston rod 169 preferably horizontally reciprocates within a piston chamber of a cylinder 168. The cylinder 168 is mounted to a mounting member 162b by a bracket member 167. A pair of rod members 163 are also slidably connected to the plate member 165 and the mounting member 162b. The mounting member 162b is then secured to a vertical support member 162a extending generally parallel to the base member 101.

The mounting arrangement of the toe inspector 160 as illustrated in FIGS. 15–17 provides a scanning-type motion as the light emitters 161 and the light detectors 166 horizontally travel along the toe portion T of the hosiery article H as illustrated by the phantom lines in FIGS. 15 and 17. The light detectors 166 preferably are mounted closely adjacent each other on the mounting plate 166c and extend between the pair of elongate and spaced-apart boarding members 111, 112.

As best illustrated in FIGS. 2 and 3, the hosiery inspecting and grading apparatus 30 has grading and sorting means 130 positioned downstream from the optical inspecting means for grading and sorting inspected pantyhose H into predetermined quality groups. The grading and sorting means 130 preferably includes means positioned adjacent to at least one boarding member 111, 112 for removing and receiving pantyhose M mounted thereon. The removing and receiving means preferably includes a manifold 131 positioned to received an inspected hosiery article H. The manifold 131 preferably includes a cavity or chamber having an upper opening positioned closely adjacent the pair of boarding members 111, 112 so that the entire hosiery article H may be received therein. A plurality of tubes 132, 133, 134 is connected to the manifold 131 along a lower end portion 135 thereof and is arranged to Sort an inspected hosiery article H into various quality levels or groups responsive electrical signals received from the controller 90. The plurality of tubes 132, 133, 134 preferably comprise three tubes as illustrated, but may comprise two or more, i.e., five, six, seven, etc., tubes for various quality categories according to the present invention.

A pneumatic device 150 such as a vacuum blower or source, preferably a high cubic feet per minute vacuum blower, is connected to the tubes 132, 133, 134 and preferably arranged to provide a vacuum-type removal of an inspected hosiery article H mounted on the boarding members 111, 112 through a main tube 146 and a plurality of respective tubes 147, 148, 149 which respectively are connected to the first plurality of tubes 132, 133, 134 at respective discharge gates 137, 138, 139. Each of the discharge gates 137, 138, 139 also have a pivoting gate member 137a, 138a, 139a which pivotally opens to discharge the inspected and graded hosiery article H into a corresponding quality group, i.e., first quality 80, irregulars 70, waste 60, as illustrated by the arrows.

Based on the predetermined quality level detected by the optical inspecting means, one of the tubes 147, 148, 149 corresponding to that quality level, i.e., first quality 80, irregulars 70, waste 60, will then have vacuum pressure applied thereto responsive to opening one of a plurality of corresponding valve gates 142, 143, 144 connected to the tubes 147, 148, 149. The valve gates 142, 143, 144 are also electrically connected to the controller 90 so that the removed hosiery article H received into the cavity of the manifold 131 is responsively drawn and sorted into the appropriate tube 132, 133, 134 and to the corresponding discharge gate 137, 138, 139. Each of the valve gates 142, 143, 144 has a corresponding valve member 142a, 143a, 144a which opens or shuts responsive to electrical signals representative of commands received from the controller 90 to either prevent or allow vacuum pressure from the vacuum source 50 to pass through the corresponding tube 132, 133, 134 directly connected to the manifold 131.

As the inspected hosiery article H passes through the selected tube 132, 133, 134 it preferably is also counted by a corresponding counter 141a, 141b, 141c connected to the selected tube 132, 133, 134. The sorting and counting of the grading and sorting means 130 further provides quality control feedback to the operator O on the number and quality of articles inspected. The removal of the inspected hosiery article H may be further assisted by the counter-clockwise rotation of the mounting belts 115a, 115b of the boarding members 111, 112. A hosiery inspecting and grading apparatus 30 according to the present invention may also further include means 200, 250 positioned downstream from the grading and sorting means 130 for receiving, boarding, and packaging an inspected and graded hosiery article H once the article is transported through the grading and sorting means 130 (see FIG. 2).

Additionally, as illustrated in FIGS. 3 and 7–17, methods of inspecting and grading a completed hosiery article H are provided according to the present invention. A method of inspecting a completed hosiery article H preferably includes emitting light through a portion of a completed hosiery article H mounted on a translucent boarding member 111, 112. The presence or absence of light emitted through the portion of a completed hosiery article R is then detected so that presence and absence of defects D in a completed hosiery article M are thereby determined.

A method of inspecting and grading a completed hosiery article H according to the present invention preferably further includes mounting a leg L of a completed hosiery article H onto a translucent and elongate boarding member 111, 112. Light is then emitted through the boarding member 111, 112 and a portion of the leg L, a gusset portion G, or a toe portion T of the completed hosiery article H mounted thereon. Light emitted through the boarding member 111, 112 and the portion of the leg L, the gusset portion G, or the toe portion T of the completed hosiery article M mounted thereon preferably is received such as by a light detector 126. The completed hosiery article H is then graded and sorted into predetermined quality groups responsive to the received light.

Although the invention is particularly well adapted to the processing of completed, i.e., knitting and/or sewing finished prior to packaging, hosiery garments such as knit leotards, pantyhose, tights, stockings, or the like, sometimes referred to above generally as pantyhose or panty garments, the invention is not limited to use in the production of such completed garments or hosiery articles H, but rather may have general application in the production, handling, and packaging of various articles. Thus, although the invention has been described more particularly herein with specific reference to stockings and pantyhose H, this reference is for convenience of description of a preferred embodiment only, and it is understood that the invention is not so limited.

In the drawings and specification, there have been disclosed a typical preferred embodiment of the invention, and although specific terms are employed, the terms are used in a descriptive sense only and not for purposes of limitation. The invention has been described in considerable detail with specific reference to this illustrated embodiment. It will be apparent, however, that various modifications and changes can be made within the spirit and scope of the invention as described in the foregoing specification and as defined in the appended claims.

That which is claimed is:

1. A hosiery inspecting and grading apparatus for inspecting and grading a completed hosiery article, the apparatus comprising:

means for mounting a completed hosiery article thereon, said mounting means being formed of a translucent material;

optical inspecting means positioned adjacent said mounting means for inspecting predetermined portions of a completed hosiery article mounted on said mounting means, said optical inspecting means including at least one light emitter positionally aligned with a portion of said mounting means to emit light through a predetermined portion of a completed hosiery article mounted thereon and at least one light detector positionally aligned with said at least one light emitter and the portion of said mounting means to detect either the presence or absence of light traveling from said light emitter and through the predetermined portion of a completed hosiery article mounted on said mounting means so that presence and absence of defects in a completed hosiery article are thereby determined; and means positioned downstream from said mounting means and said optical inspecting means and in electrical communication with said optical inspecting means for grading and sorting a completed hosiery article into one of at least three predetermined quality groups responsive to the presence or absence of defects detected by said optical inspecting means.

2. A hosiery inspecting and grading apparatus as defined by claim 1, wherein said grading and sorting means includes means positioned adjacent said mounting means for removing and receiving an inspected and graded hosiery article from said mounting means.

3. A hosiery inspecting and grading apparatus as defined by claim 2, further comprising means positioned downstream from said grading and sorting means for receiving and packaging an inspected and graded hosiery article.

4. A hosiery inspecting and grading apparatus as defined by claim 2, further comprising means in electrical communication with said optical inspecting means and said grading and sorting means for controlling said grading and sorting means responsive to electrical signals received from said optical inspecting means.

5. A hosiery inspecting and grading apparatus as defined by claim 4, wherein said mounting means comprises at least one elongate boarding member positioned to mount a leg of a hosiery article thereon, and wherein said at least one light emitter and said at least one light detector of said optical inspecting means are mounted to reciprocate upwardly and downwardly along a leg of a completed hosiery article.

6. A hosiery inspecting and grading apparatus as defined by claim 4, wherein said at least one light emitter and said at least one light detector of said optical inspecting means respectively comprise a first light emitter and a first light detector positioned to inspect a first predetermined portion of a completed hosiery article, and wherein said optical inspecting means further includes a second light emitter and a second light detector positioned to inspect a second predetermined portion of a completed hosiery article and a third light emitter and a third light detector positioned to inspect a third predetermined portion of a completed hosiery article.

7. A hosiery inspecting and grading apparatus as defined by claim 6, wherein said mounting means comprises a pair of elongate and spaced-apart boarding members respectively positioned to mount a pair of legs of a completed hosiery article thereon, and wherein said first light emitter and said first light detector of said optical inspecting means are mounted to reciprocate upwardly and downwardly along at least one of the pair of legs of the hosiery article mounted on said pair of elongate boarding members.

8. A hosiery inspecting and grading apparatus as defined by claim 7, wherein said second light emitter and said second light detector are positioned to reciprocate along a gusset portion positioned between a pair of legs of a completed hosiery article mounted on said elongate and spaced-apart boarding members, and wherein said third light emitter and said third light detector are positioned to reciprocate along at least one toe portion of a completed hosiery article mounted on said pair of elongate and spaced-apart boarding members.

9. A hosiery inspecting and grading apparatus as defined by claim 1, further comprising means in electrical communication with said at least one light detector for storing data representative of defects in a hosiery article.

10. A hosiery inspecting and grading apparatus for inspecting and grading a completed hosiery article, the apparatus comprising:
   a boarding member positioned to mount a completed hosiery article thereon, said boarding member being formed of a translucent material;
   a light emitter positionally aligned with said boarding member to emit light through a predetermined portion of a completed hosiery article mounted thereon;
   a light detector positionally aligned with said light emitter and said boarding member to detect either presence or absence of light traveling from said light emitter and through the predetermined portion of a completed hosiery article mounted on said boarding member;
   a controller in electrical communication with said light detector and arranged to determine the presence and absence of defects in a predetermined portion of a completed hosiery article responsive to electrical signals representative of the presence or absence of light received from said light detector; and
   means positioned downstream from said light emitter and said light detector for grading and sorting an inspected hosiery article into one of at least three predetermined quality groups.

11. A hosiery inspecting and grading apparatus as defined by claim 10, wherein said grading and sorting means includes means positioned adjacent said mounting means for removing and receiving an inspected hosiery article from said mounting means, said removing and receiving means comprising a manifold positioned to received an inspected hosiery article therein, a plurality of tubes connected to said manifold and positioned to sort an inspected hosiery article responsive to said controller, and a pneumatic device connected to said tubes and arranged to provide a pressurized removal of an inspected hosiery article mounted on said boarding member.

12. A hosiery inspecting and grading apparatus as defined by claim 13, further comprising means positioned downstream from said grading means for receiving and packaging an inspected and graded hosiery article.

13. A hosiery inspecting and grading apparatus as defined by claim 12, wherein said mounting means comprises at least one elongate boarding member having front and back surfaces positioned to mount a leg of a completed hosiery article thereon, and wherein said light emitter and said light detector of said optical inspecting means are mounted to reciprocate upwardly and downwardly along the front and back surfaces of said elongate boarding member and along a leg of a completed hosiery article mounted thereon.

14. A hosiery inspecting and grading apparatus as defined by claim 12, wherein said light emitter and said light detector of said optical inspecting means respectively comprise a first light emitter and a first light detector positioned to inspect a first predetermined portion of a completed hosiery article, and wherein said optical inspecting means further includes a second light emitter and a second light detector positioned to inspect a second predetermined portion of a completed hosiery article and a third light emitter and a third light detector positioned to inspect a third predetermined portion of a hosiery article.

15. A hosiery inspecting and grading apparatus as defined by claim 14, wherein said mounting means comprises a pair of elongate and spaced-apart boarding members respectively positioned to mount a pair of legs of a completed hosiery article thereon, and wherein said first light emitter and said first light detector of said optical inspecting means are mounted to vertically reciprocate along at least one of the pair of legs of the completed hosiery article mounted on said pair of elongate boarding members.

16. A hosiery inspecting and grading apparatus as defined by claim 15, wherein said second light emitter and said second light detector are positioned to reciprocate along a gusset portion positioned between a pair of legs of a completed hosiery article mounted on said elongate and spaced-apart boarding members, and wherein said third light emitter and said third light detector are positioned to reciprocate along at least one toe portion of a completed hosiery product mounted on said pair of elongate and spaced-apart boarding members.

17. A hosiery inspecting and grading apparatus as defined by claim 10, further comprising a computer in electrical communication with said controller for storing and processing data representative of defects in a hosiery article.

18. A hosiery inspecting and grading apparatus for inspecting and grading a completed hosiery article, the apparatus comprising:
   a base member;
   a plurality of pairs of elongate and spaced-apart boarding members having upper portions thereof mounted to rotate about an upper portion of said base member, each said pair of elongate and spaced-apart boarding members extending downwardly from the upper portion of said base member and respectively positioned to mount a pair of legs of a completed pantyhose thereon so that a gusset portion of the completed pantyhose extends between said pair of elongate and spaced-apart boarding members, each of said boarding members being formed of a translucent material;

a first light emitter positionally aligned with at least one of said boarding members and positioned to vertically travel generally parallel to a front surface of said boarding member to emit light onto and through the front surface of said boarding member and a portion of a leg of a completed pantyhose when mounted thereon;

a first light detector positionally aligned with said first light emitter and said at least one of said plurality of boarding members and positioned to vertically travel generally parallel to a back surface of said at least one elongate boarding member to detect the presence and absence of light traveling from said light emitter and through said boarding member and the portion of a leg of a completed pantyhose mounted thereon so that presence and absence of defects in the completed pantyhose mounted on said boarding member are thereby determined;

a second light emitter arranged to emit light through a gusset portion extending between a pair of legs of pantyhose mounted on said pair of boarding members;

a second light detector positionally aligned with said second light emitter and arranged to detect light traveling from said second light emitter and through a gusset portion of a completed pantyhose so that presence and absence of defects in the gusset portion are thereby determined;

a controller in electrical communication with said first and second light emitters and said first and second light detectors and arranged to determine the presence and absence of defects in at least a leg and a gusset portion of a completed pantyhose responsive to electrical signals representative of the presence or absence of light received from said first and second light detectors; and means positioned downstream from said first and second light emitters and said first and second light detectors for grading and sorting inspected pantyhose into one of at least three predetermined quality groups, said grading and sorting means including means positioned adjacent to said pair of boarding members for removing and receiving a completed pantyhose mounted thereon.

19. A hosiery inspecting and grading apparatus as defined by claim 18, wherein said grading and sorting means includes means positioned adjacent said mounting means for removing and receiving an inspected hosiery article from said mounting means, said removing and receiving means comprising a manifold positioned to received an inspected hosiery article therein, a plurality of tubes connected to said manifold and positioned to sort an inspected hosiery article responsive to said controller, and a pneumatic device connected to said tubes and positioned to provide a pressurized removal of an inspected hosiery article mounted on said boarding member.

20. A hosiery inspecting and grading apparatus as defined by claim 19, further comprising means positioned downstream from said grading and sorting means for receiving and packaging an inspected and graded hosiery article.

21. A hosiery inspecting and grading apparatus as defined by claim 20, further comprising a third light emitter positioned to emit light through a toe portion of a leg of a completed pantyhose mounted on said boarding member and a third light detector positionally aligned with said third light emitter and positioned to detect light traveling from said third light emitter and through said boarding member and a toe portion of a completed pantyhose mounted thereon so that presence and absence of defects in the toe portion are thereby determined.

22. A method of inspecting and grading a hosiery article comprising:

emitting light through a predetermined portion of a completed hosiery article mounted on a translucent boarding member;

detecting either the presence or absence of light traveling through the predetermined portion of a completed hosiery article mounted on the translucent boarding member so that presence and absence of defects in a completed hosiery article are thereby determined and grading and sorting a completed hosiery article into one of at least three predetermined quality group responsive to detecting the presence or absence of light.

23. A method of inspecting and grading a hosiery article as defined by claim 22, further comprising storing data representative of defects in an inspected hosiery article responsive to the presence or absence of light.

24. A method of inspecting and grading a hosiery article comprising:

mounting a leg of a completed hosiery article onto a translucent and elongate boarding member;

emitting light through the boarding member and the leg of the hosiery article mounted thereon;

receiving light emitted through the boarding member and the leg of the hosiery article mounted thereon; and grading and sorting the hosiery article into one of at least three predetermined quality groups responsive to the received light.

25. A method of inspecting and grading a hosiery article comprising:

mounting a pair of legs of a completed hosiery article onto a pair of elongate and spaced-apart boarding members so that a gusset portion of the completed hosiery article extends between the elongate and spaced-apart boarding members when the pair of legs are mounted thereon;

emitting light through the gusset portion of the mounted hosiery article;

receiving light emitted through the gusset portion of the mounted hosiery article; and grading and sorting the hosiery article into one of at least three predetermined quality groups responsive to the received light.

26. A method of inspecting and grading a hosiery article comprising:

mounting a pair of legs of a completed hosiery article onto a pair of elongate and spaced-apart boarding members so that a gusset portion of the completed hosiery article extends between the elongate and spaced-apart boarding members when the pair of legs are mounted thereon, the elongate and spaced-apart boarding members each being formed of a translucent material;

emitting light respectively through the gusset portion, the legs, and toe portions of the legs of the mounted hosiery article;

receiving light emitted respectively through the gusset portion, the legs, and toe portions of the legs of the mounted hosiery article; and grading and sorting the hosiery article into one of at least three predetermined quality groups responsive to the received light.

* * * * *

UNITED STATES PATENT AND TRADEMARK OFFICE
CERTIFICATE OF CORRECTION

PATENT NO. : 5,497,235

DATED : March 5, 1996

INVENTOR(S) : Bell

It is certified that error appears in the above-identified patent and that said Letters Patent is hereby corrected as shown below:

On the title page, item [56],

For reference 4,656,463, "Anders" should be --Anders et al.-- .

In the ABSTRACT:

Line 2, "has" should be --have--.

Column 5, line 34, "space-apart" should be --spaced-apart--;

line 54, "for" should be --form--;

line 55, between "or" and "positioned" insert --be--.

Column 6, line 14, after ratus, insert --.-- .

Column 8, line 17, "dispose" should be --disposed--;

line 22, "Or" should be --or--;

line 23, "vertically" should be --vertical--.

Column 9, line 28, "dispose" should be --disposed--;

line 34, "vertically" should be --vertical.

UNITED STATES PATENT AND TRADEMARK OFFICE
CERTIFICATE OF CORRECTION

PATENT NO. : 5,497,235
DATED : March 5, 1996
INVENTOR(S) : Bell

It is certified that error appears in the above-identified patent and that said Letters Patent is hereby corrected as shown below:

Column 10, line 11, "dispose" should be --disposed--;

line 50, "M" should be --H--;

line 52, "received" should be --receive--;

line 59, between "responsive" and "electrical" insert --to--.

Column 11, line 65, "M" should be --H--.

Column 14, line 8, "received" should be --receive--;

line 16, "claim 13" should be --claim 11--.

Column 15, line 55, "received" should be --receive--.

Column 16, line 16, after "determined" insert --;--;

UNITED STATES PATENT AND TRADEMARK OFFICE
CERTIFICATE OF CORRECTION

PATENT NO. : 5,497,235
DATED : March 5, 1996
INVENTOR(S) : Bell

It is certified that error appears in the above-indentified patent and that said Letters Patent is hereby corrected as shown below:

Column 16, line 18, "group" should be --groups--.

Signed and Sealed this

Twenty-fifth Day of June, 1996

Attest:

BRUCE LEHMAN

*Attesting Officer*  *Commissioner of Patents and Trademarks*